(12) United States Patent
Benary et al.

(10) Patent No.: US 11,350,953 B2
(45) Date of Patent: Jun. 7, 2022

(54) IMPACTOR FOR FRACTURING CALCIFICATIONS IN HEART VALVES

(71) Applicant: Pi-Cardia Ltd., Rehovot (IL)

(72) Inventors: Raphael Benary, Tel Aviv (IL); Erez Golan, Rehovot (IL); Ofir Gal-Or, Rehovot (IL)

(73) Assignee: Pi-Cardia Ltd., Rehovot (IL)

( * ) Notice: Subject to any disclaimer, the term of this patent is extended or adjusted under 35 U.S.C. 154(b) by 87 days.

(21) Appl. No.: 16/894,999

(22) Filed: Jun. 8, 2020

(65) Prior Publication Data
US 2020/0297361 A1 Sep. 24, 2020

Related U.S. Application Data

(63) Continuation of application No. 15/766,830, filed as application No. PCT/IB2016/055993 on Oct. 6, 2016, now Pat. No. 10,675,044.

(60) Provisional application No. 62/238,250, filed on Oct. 7, 2015.

(51) Int. Cl.
*A61B 17/22* (2006.01)
*A61B 17/3207* (2006.01)
*A61B 17/00* (2006.01)

(52) U.S. Cl.
CPC .......... *A61B 17/22* (2013.01); *A61B 17/3207* (2013.01); *A61B 17/00234* (2013.01); *A61B 2017/22098* (2013.01)

(58) Field of Classification Search
CPC .......... A61B 17/3207; A61B 17/00234; A61B 17/22; A61B 2017/22098; A61B 17/22031; A61B 17/221; A61B 2017/2212; A61B 2017/2215; A61B 17/320725
See application file for complete search history.

(56) References Cited

U.S. PATENT DOCUMENTS

| | | | | |
|---|---|---|---|---|
| 6,030,406 A | * | 2/2000 | Davis | A61B 17/00008 604/104 |
| 2011/0184447 A1 | * | 7/2011 | Leibowitz | A61B 17/320016 606/170 |
| 2015/0216552 A1 | * | 8/2015 | Hefer | A61M 25/104 606/159 |

* cited by examiner

*Primary Examiner* — Wade Miles
*Assistant Examiner* — Andrew P. Restaino
(74) *Attorney, Agent, or Firm* — Dekel Patent Ltd.; David Klein

(57) ABSTRACT

A device for fracturing calcifications in heart valves includes a tube formed with at least two longitudinal slits that form at least two struts. Each of the struts includes two or more pairs of notches formed on opposite sides of the strut. The struts have a contracted orientation in which the struts are not expanded outwards from the tube and an outwardly expanded orientation in which the struts are expanded outwards from the tube and have sufficient strength and rigidity to impact and fracture a calcification in a heart valve.

17 Claims, 4 Drawing Sheets

IMPACTOR FOR FRACTURING CALCIFICATIONS IN HEART VALVES

FIELD OF THE INVENTION

The present invention generally relates to devices and methods for fracturing calcifications in heart valves, such as aortic valve leaflets.

BACKGROUND OF THE INVENTION

PCT Patent Applications PCT/US2010/058810 and PCT/US2012/067812, assigned to the present assignee, describe devices for fracturing calcifications in heart valves. The device includes a catheter that has an expandable stabilizer, an impactor shaft and an internal shaft, all disposed in an external shaft. Expandable impactor arms are mounted on the impactor shaft. The internal shaft is movable to cause the impactor arms to expand outwards and be locked in an expanded shape. An impacting element is movable to cause the impactor arms, while in the expanded shape, to move towards the tissue with sufficient energy so as to fracture a calcification located in tissue which is fixed by the stabilizer in a certain position vis-à-vis the impactor arms. The internal shaft may be lockable relative to the impactor shaft so that the impactor arms are fixed.

A brief description of using the device is as follows. The catheter may be delivered over a guide-wire through a blood vessel, such as the peripheral artery, using a retrograde approach, through the aortic arch and into the ascending aorta, just above the aortic valve. The external shaft is retracted so that the expandable stabilizer expands and opens up. The stabilizer is used to guide, position and anchor the catheter distal part in the sinuses, just above the valve leaflets. An impactor shaft, including folded impactor arms, is then pushed forward (distally) through the center of the valve into the left ventricle. When pushed forward the impactor arms are folded so that they can easily cross the valve. The internal shaft is then pulled proximally to cause the impactor arms to open (expand) outwards sideways and lock them in the expanded shape. The impactor and internal shafts are manipulated so that the leaflets are "sandwiched" between the stabilizer (which may make contact with the leaflets from the aortic aspect) and the impactor arms (which may make contact with the leaflets from the ventricular aspect, or vice versa). In order to fracture leaflet calcifications, the impactor arms are pulled abruptly towards the leaflet tissue to impact the calcification, with the stabilizer serving as an anvil.

In one embodiment, the impactor has struts in a Y-shape (separated from each other at about 120°) and/or other struts which can be used in various rotational positions on the valve, such as on the ventricular aspect of the commissures or the centerline of the valve's leaflets. The structure of the impactor enables active self-positioning of the device on the aortic valve. For example, proximal structural struts are located higher than and at an angle relative to the impaction struts, so that the proximal structural struts position themselves just below the commissures when the impactor is pulled towards the valve.

The impaction struts and stabilizer are shaped in accordance with a shape of the desired fracture site, e.g., leaflet bases (close to the annulus) and central folding lines of the native valve. Accordingly, the shapes of the impaction struts and of the stabilizer may include portions with a bicuspid shape, a tricuspid shape, or a semilunar shape, and may additionally have a portion with a depression corresponding to the folding lines, depending on the valve to be treated. Due to these predetermined shapes, the impactor, by impacting against the stabilizer, is able to generate fractures along the leaflet bases (close to the annulus) and central folding lines of the valve.

The various impactor designs may be used to increase the open cross-sectional area of the valve during systole. In this method the impactor is inserted in a fully or partially closed configuration through the valve in between the valve's leaflets and then is gradually dilated to increase the open cross-sectional area of the valve. This method may be used before or after impact has been delivered to the leaflets to increase the effect of valve fractures on leaflet pliability, or without delivering impact to the valve. Impactor dilation of the valve may enlarge present fractures, create new fractures, stretch the valve and its immediate surroundings, separate fused commissures and soften calcific deposits within the valve.

The system can make pressure measurements from the ventricular and aortic aspects of the aortic valve.

SUMMARY OF THE INVENTION

The present invention seeks to provide further impactor devices that may be used for fracturing calcifications in aortic valve leaflets, in order to increase leaflet pliability and mobility, either as standalone treatment, bridge treatment or preparation of the "landing zone" for trans-catheter valve implantation.

The term "fracture" refers to any kind of reduction in size or any modification in shape or form, such as but not limited to, fracturing, pulverizing, breaking, grinding, chopping and the like.

There is provided in accordance with an embodiment of the invention a device for fracturing calcifications in heart valves including a tube formed with at least two longitudinal slits that form at least two struts, each of the struts including two or more pairs of notches formed on opposite sides of the strut, the struts having a contracted orientation in which the struts are not expanded outwards from the tube and an outwardly expanded orientation in which the struts are expanded outwards from the tube and have sufficient strength and rigidity to impact and fracture a calcification in a heart valve. A curved waist portion may extend between two longitudinally-spaced pairs of the notches, wherein in the outwardly expanded orientation, the waist portions are curved radially inwards.

In accordance with a non-limiting embodiment of the invention the waist portion is made from a scored or weakened portion of the strut.

In accordance with a non-limiting embodiment of the invention pairs of the notches are formed at different locations along a longitudinal length of the strut. The struts may or may not be symmetrically separated from each other.

In accordance with a non-limiting embodiment of the invention the waist portion is shaped to conform to a ventricular side of a valve leaflet.

In accordance with a non-limiting embodiment of the invention a distal end and a proximal end of the tube are affixed to an inner tube and an outer tube, respectively, of an actuator for expanding or contractiong the struts.

There is provided in accordance with a non-limiting embodiment of the invention a method for fracturing calcifications in heart valves including introducing the abovementioned device to a valve and expanding the struts against a calcification located in the valve so as to fracture the calcification.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
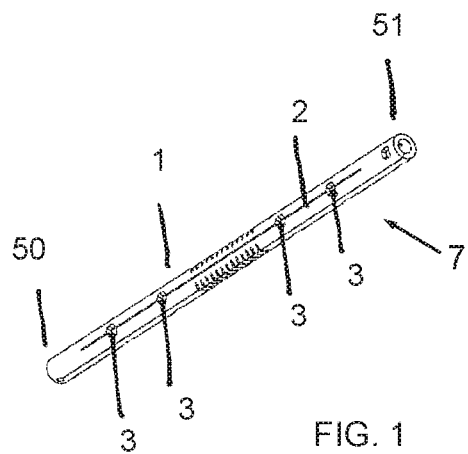
FIG. 1 is a simplified illustration of an impactor, in a completely contracted orientation, in accordance with a non-limiting embodiment of the invention.

Reference is now made to FIG. 1, which illustrates an impactor device 7, in accordance with a non-limiting embodiment of the invention.

The device 7 includes a tube 1 formed with at least two longitudinal slits 2, cut or ohterwise formed through a thickness of the tube 1 for most, but not all, of the tube length. The material left between adjacent slits forms a strut 4. One or more transverse cuts 3 extend circumferentially from each slit 2 so as to form one or more notches 3 in the struts 4. In the non-limiting illustrated embodiment, there are three struts 4 (which may be symmetrically separated from each other by 120° or may be non-symmetrically separated from each other by different angular spacings). Each strut has two or more pairs of notches 3 on opposite sides of the strut at different locations along the longitudinal length of the strut. Each strut can be split along its longitudinal length (either at the center or off-center) to form two struts and thus increase contact locations with the cardiac tissue.

The assembly can be made from nitinol or stainless steel or any other suitable material. The struts may include a curved waist portion 5, made from a scored or weakened portion of the strut. The waist 5 may be shaped to conform to the ventricular side of a valve leaflet 21 (seen in FIGS. 5-7). The waist 5 extends between two longitudinally-spaced pairs of notches 3.

Figure 2:
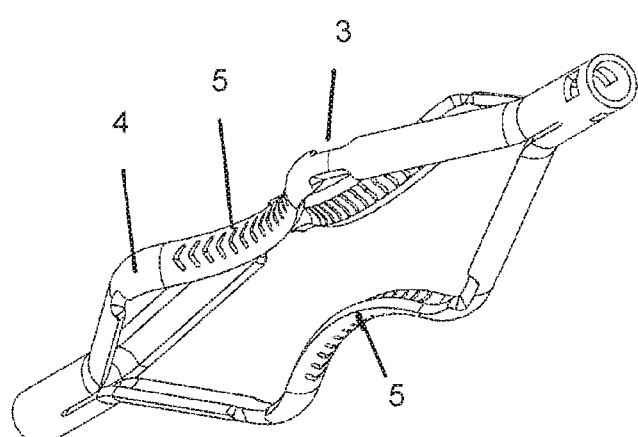
FIGS. 2 and 3 are simplified illustrations of the impactor, in two different expanding orientations, in accordance with a non-limiting embodiment of the invention.
Figure 3:
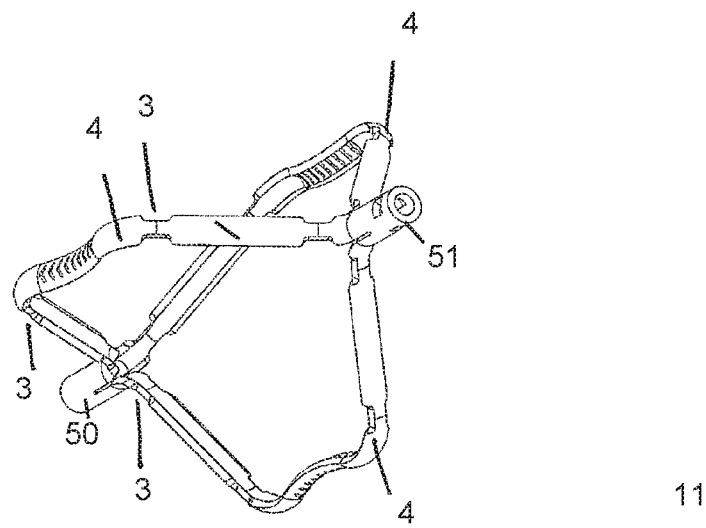

FIGS. 2 and 3 show device 7 with the struts 4 deployed outwards at varying amounts of outward expansion. It is seen that when struts 4 are in the outwardly expanded orientation, waists portions 5 are curved radially inwards.

Figure 4:
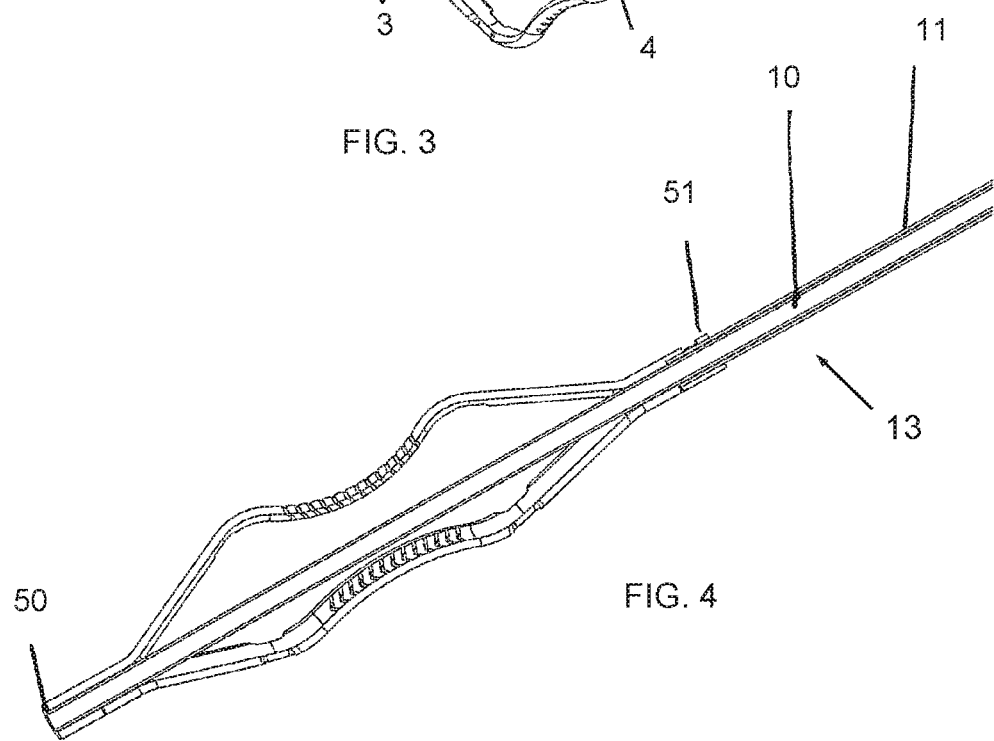
FIG. 4 is a simplified partially sectional illustration of the impactor assembled on an actuator for expanding or contracting the impactor, in accordance with a non-limiting embodiment of the invention.

Reference is now made to FIG. 4. A distal end 50 and a proximal end 51 of the tube 1 of device 7 are affixed to an inner tube 10 and an outer tube 11, respectively, of an actuator 13 for expanding or contractiong the struts 4. Moving the inner tube 10 proximally with respect to the outer tube 11 causes the struts 4 to expand outwards; conversely, moving the inner tube 10 distally with respect to the outer tube 11 causes the struts 4 to contract inwards. Alternatively, moving the outer tube 11 distally with respect to the inner tube 10 causes the struts 4 to expand outwards; conversely, moving the outer tube 11 proximally with respect to the inner tube 10 causes the struts 4 to contract inwards.

Figure 5:
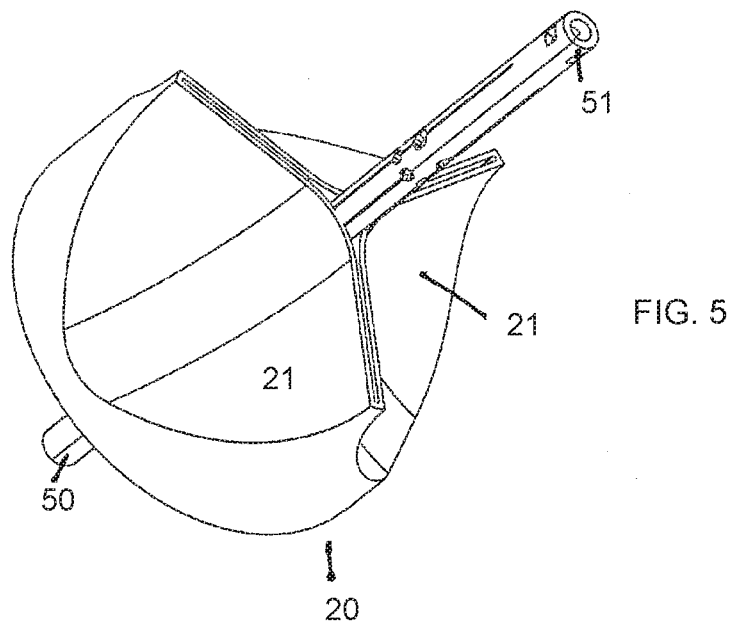
FIGS. 5-7 are simplified illustrations of introducing the impactor to the site of a valve and valve leaflets, respectively, with the impactor contracted, partially expanded and fully expanded at the valve site.
Figure 6:
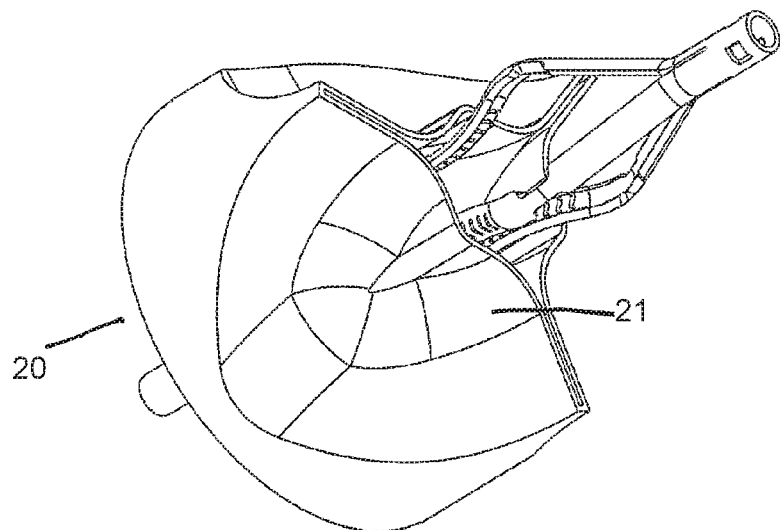
Figure 7:
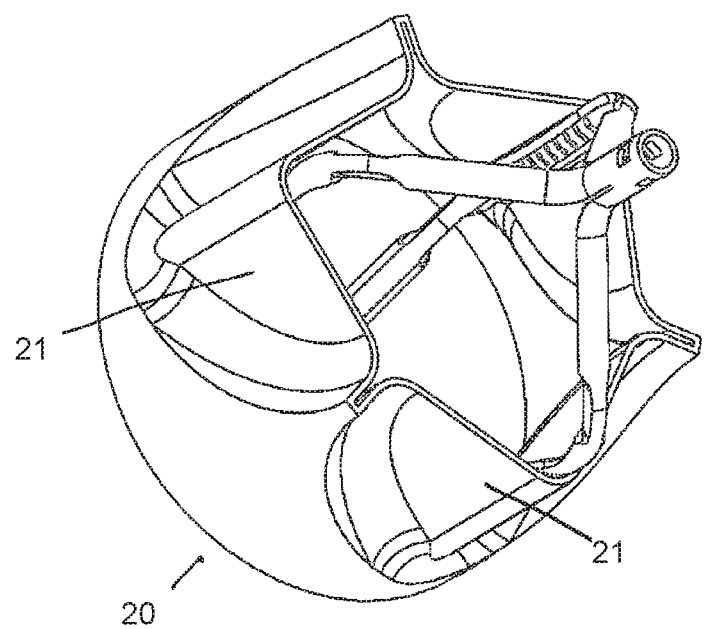

Reference is now made to FIGS. 5-7, which illustrate introducing the impactor to the site of a valve 20 (e.g., the aortic valve) and valve leaflets 21.

The impactor device 7 is initially contracted and may be placed in a catheter with a protective sheath or any other delivery device (not shown). The delivery device may be used to deliver the contracted impactor device 7 through the vasculature, such as the peripheral artery through the aortic arch and into the ascending aorta, through the aortic valve and finally into the left ventricle. The actuator 13 (not shown here) is then manipulated to partially expand (FIG. 6) and then fully expand (FIG. 7) the struts 4 of the impactor 7 at the valve site. The operator can control the amount of outward expansion by manipulating the actuator 13. Varying the degree of expansion modifies the impact force the impactor 7 can apply to calcifications. The struts 4 can be optionally vibrated as they expand to increase the efficiency of the impacts to break calcifications. As in PCT Patent Applications PCT/US2010/058810 and PCT/US2012/067812, a stabilizer (not shown) can be used on the other side of the leaflets for bearing the force of the impacts.

In the expanded orientation, the struts have sufficient strength and rigidity to impact and fracture calcifications. For example, without limitation, a material with an elastic modulus of at least 20 GPa and/or yield strength of at least 70 MPa will have sufficient strength and rigidity to impact and fracture calcifications.

What is claimed is:

1. A device for fracturing calcifications in heart valves, the device comprising:

an impactor comprising a plurality of struts, a proximal tube at a proximal region of the impactor, and a distal tube at a distal region of the impactor, wherein the proximal tube is configured to move relative to the distal tube to transition the impactor from a contracted orientation in which the plurality of struts form a tubular shape along a longitudinal axis of the impactor to an expanded orientation in which the plurality of struts are expanded radially outward from the longitudinal axis of the impactor to conform to a side of one or more native leaflets of a calcified heart valve and exhibit force on the side of the one or more native leaflets in a direction towards an opposing side of the one or more native leaflets to fracture calcifications on the one or more native leaflets, and wherein, in the expanded orientation, the plurality of struts bend inward toward the longitudinal axis of the impactor to conform to the side of one or more native leaflets.

2. The device of claim 1, wherein, in the expanded orientation, the plurality of struts are expanded radially outward from the longitudinal axis of the impactor to conform to a ventricular side of one or more native leaflets of the calcified heart valve.

3. The device of claim 1, wherein the plurality of struts each comprise one or more notches positioned between the proximal region and the distal region of the impactor.

4. The device of claim 3, wherein the plurality of struts each comprise two notches formed on opposite sides of the plurality of struts.

5. The device of claim 4, wherein the plurality of struts each comprise a curved waist portion extending between the two notches.

6. The device of claim 5, wherein the curved waist portion of the plurality of struts comprises a scored or weakened portion of the plurality of struts.

7. The device of claim 5, wherein, in the expanded orientation, the curved waist portion of the plurality of struts conforms to the side of one or more native leaflets of the calcified heart valve.

8. The device of claim 1, wherein each of the plurality of struts are symmetrically separated from each other.

9. The device of claim 1, wherein each of the plurality of struts are non-symmetrically separated from each other.

10. The device of claim 1, wherein the plurality of struts are formed from a tube having at least two longitudinal slits.

11. The device of claim 1, wherein the proximal tube is configured to move relative to the distal tube to transition the impactor from the contracted orientation to a first expanded orientation in which the plurality of struts are partially expanded radially outward from the longitudinal axis of impactor, and wherein the proximal tube is further configured to move relative to the distal tube to transition the impactor from the first expanded orientation to a second expanded orientation in which the plurality of struts are fully expanded radially outward from the longitudinal axis of the impactor to exhibit force on the side of one or more native leaflets.

12. The device of claim 1, further comprising an actuator operatively coupled to the proximal tube and the distal tube of the impactor, the actuator configured to move the proximal tube relative to the distal tube.

13. A method for fracturing calcifications in heart valves, the method comprising:
   positioning an impactor comprising a plurality of struts adjacent to one or more native leaflets of a calcified heart valve, the impactor further comprising a proximal tube at a proximal region of the impactor and a distal tube at a distal region of the impactor;
   moving the proximal tube relative to the distal tube to transition the impactor from a contracted orientation in which the plurality of struts form a tubular shape along a longitudinal axis of the impactor to an expanded orientation in which the plurality of struts are expanded radially outward from the longitudinal axis of the impactor to conform to a side of the one or more native leaflets of the calcified heart valve; and
   exhibiting a force on the side of the one or more native leaflets via the plurality of struts in a direction towards an opposing side of the one or more native leaflets, thereby fracturing calcifications on the one or more native leaflets, wherein, in the expanded orientation, the plurality of struts bend inward toward the longitudinal axis of the impactor to conform to the side of one or more native leaflets.

14. The method of claim 13, wherein moving the proximal tube relative to the distal tube comprises actuating an actuator operatively coupled to the proximal tube and the distal tube of the impactor.

15. The method of claim 13, wherein, in the expanded orientation, the plurality of struts are expanded radially outward from the longitudinal axis of the impactor to conform to a ventricular side of one or more native leaflets of the calcified heart valve.

16. The method of claim 13, further comprising moving the proximal tube relative to the distal tube to transition the impactor from the contracted orientation to a first expanded orientation in which the plurality of struts are partially expanded radially outward from the longitudinal axis of impactor.

17. The method of claim 16, further comprising moving the proximal tube relative to the distal tube to transition the impactor from the first expanded orientation to a second expanded orientation in which the plurality of struts are fully expanded radially outward from the longitudinal axis of the impactor to exhibit force on the side of one or more native leaflets.

* * * * *